United States Patent [19]

Rajagopalan et al.

[11] Patent Number: 5,623,077
[45] Date of Patent: Apr. 22, 1997

[54] IMIDAZOLE BASED NITROGEN SULFUR LIGANDS USEFUL IN RADIOGRAPHIC IMAGING AGENTS

[75] Inventors: Raghavan Rajagopalan, Maryland Heights; Ananthachari Srinivasan, St. Charles, both of Mo.

[73] Assignee: Mallinckrodt Medical, Inc., St. Louis, Mo.

[21] Appl. No.: 420,612

[22] Filed: Apr. 10, 1995

Related U.S. Application Data

[63] Continuation of Ser. No. 30,940, Mar. 12, 1993, abandoned.
[51] Int. Cl.⁶ .................. C07D 233/91; A61K 51/04
[52] U.S. Cl. ..................... 548/338.1; 548/335.1
[58] Field of Search .............. 424/1.65; 548/106, 548/107, 311.1, 315.4, 338.1, 338.5

[56] References Cited

U.S. PATENT DOCUMENTS

| | | | |
|---|---|---|---|
| 4,193,979 | 3/1980 | Frank et al. | 424/1.65 |
| 4,233,310 | 11/1980 | Fujita et al. | 548/338.5 X |
| 4,339,379 | 7/1982 | Masaki et al. | 548/106 X |
| 4,965,365 | 10/1990 | Sanfeliu et al. | 548/109 |
| 5,071,636 | 12/1991 | Yamauchi et al. | 424/1.65 |
| 5,217,706 | 6/1993 | Rajagopalan et al. | 424/9 |
| 5,276,147 | 1/1994 | Thornback et al. | 424/1.65 X |
| 5,302,370 | 4/1994 | Neumeier et al. | 424/1.65 X |
| 5,330,737 | 7/1994 | Rajagopalan | 424/1.65 |
| 5,371,184 | 12/1994 | Rajagopalan et al. | 530/324 |
| 5,376,356 | 12/1994 | Morgan, Jr. | 424/1.41 |
| 5,376,357 | 12/1994 | Rajagopalan et al. | 424/9 |
| 5,382,654 | 1/1995 | Lyle et al. | 530/311 |

OTHER PUBLICATIONS

H. Sakurai et al., Chem. Pharm. Bull. 27:3022 (1979).

*Primary Examiner*—John Kight
*Assistant Examiner*—Lara Chapman Kelley
*Attorney, Agent, or Firm*—Wendell Ray Guffey; Roy J. Klostermann; Thomas P. McBride

[57] ABSTRACT

The present invention relates particularly to novel imidazole based nitrogen-sulfur ligands that are suitable for complexing with a radionuclide, and are useful as general imaging agents for diagnostic purposes.

1 Claim, No Drawings

IMIDAZOLE BASED NITROGEN SULFUR LIGANDS USEFUL IN RADIOGRAPHIC IMAGING AGENTS

This is a continuation of Ser. No. 08/030,940 filed on Mar. 12, 1993, now abandoned.

BACKGROUND OF THE INVENTION

The present invention relates to novel ligands for forming radionuclide complexes, new complexes incorporating such ligands, processes for preparing such complexes, imaging agents incorporating such complexes, and methods of imaging using such imaging agents.

The use of radiographic imaging agents for visualizing skeletal structures, organs, or tissues, is well known in the area of biological and medical research and diagnostic procedures. The procedure whereby such imaging is accomplished, generally involves the preparation of radioactive agents, which, when introduced to the biological subject, are localized in the specific skeletal structures, organs or tissues to be studied. The localized radioactive agents may then be traced, plotted or scintiphotographed by radiation detectors, such as, traversing scanners or scintillation cameras. The distribution and relative intensity of the detected radioactive agents indicates the position of the tissue in which the agent is localized, and also shows the presence of aberrations, pathological conditions or the like.

In general, the radiographic imaging agents comprise radionuclide-labelled compounds; such as complexes of technetium 99m, rhenium 186 or rhenium 188, or other applicable radionuclides; with appropriate carriers, and auxiliary agents, such as delivery vehicles suitable for injection into, or aspiration by, the patient, physiological buffers and salts, and the like.

DETAILED DESCRIPTION OF THE INVENTION

The present invention relates particularly to novel aminothiol ligands that are suitable for complexing with a radionuclide, and are useful as general imaging agents for diagnostic purposes. In particular the present invention relates to novel ligands having the general formula:

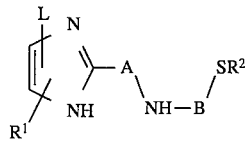

Formula (I)

wherein $R^1$ is selected from the group consisting of hydrogen, alkyl, hydroxyl, alkoxyl, hydroxyalkyl, alkoxyalkyl, alkoxycarbonyl, or carbamoyl, wherein the carbon containing portions of such group contain 1 to 10 carbon atoms; $R^2$ is a suitable sulfur protecting group selected from the group consisting of acetyl, benzoyl, methoxyacetyl, 1-3-dioxacyclohexyl, 1,3-dioxacyclopentyl, alkoxycarbonyl, carbamoyl, alkoxyalkyl, dialkoxyalkyl, tetrahydropyranyl, tetrahydrofuranyl, p-methoxybenzyl, benzhydryl, trityl, and the like; L is selected from the group consisting of

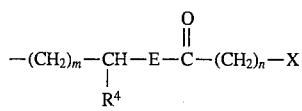

wherein k, l, m and n are 0 to 10, preferably 1 to 6, E is —O—, —S—, or —NR$^3$, wherein $R^3$ is defined in the same manner as $R^1$ above, $R^4$ is defined in the same manner as $R^1$ above, and X is a suitable coupling moiety selected from the group consisting of formyl, carboxyl, hydroxyl, amino, t-butoxycarbonylamino, chlorocarbonyl, N-alkoxycarbamoyl, succinimidyloxycarbonyl, imidate, isocyanate, isothiocyanate, tetrafluorophenoxy, and the like; A is selected from the group consisting of

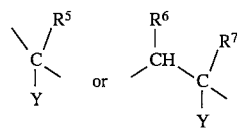

wherein $R^5$ to $R^7$ are defined in the same manner as $R^1$ above, and Y is defined in the same manner as L above; and B is selected from the group consisting of

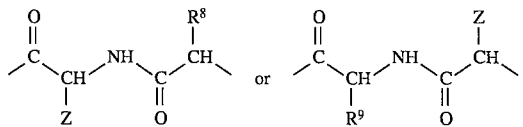

wherein $R^8$ and $R^9$ are defined in the same manner as $R^1$ above, and Z is defined in the same manner as L above.

In a preferred embodiment, ligands according to the present invention have the general Formula (I) above, wherein A is

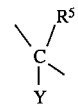

wherein $R^5$ and Y are hydrogens; B is

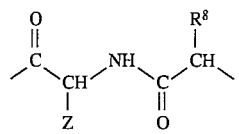

wherein $R^8$ is hydrogen and Z is a —(CH$_2$)$_k$—X group wherein k is 4 and X is an amino, or an isothiocyanato group; $R^2$ is a benzoyl or a tetrahydropyranyl group; and $R^1$ and L are hydrogen.

In another preferred embodiment, ligands according to the present invention have the general Formula (I) wherein A is

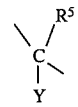

wherein R⁵ and Y are hydrogens; B is

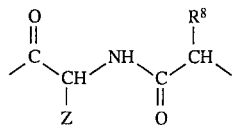

wherein R⁸ is hydrogen and Z is a —(CH₂)$_k$—X group wherein k is 2 and X is either carboxyl or hydroxyl; R² is a benzoyl or a tetrahydropyranyl group; and R¹ and L are hydrogen.

The novel ligands described above, may be incorporated into radionuclide complexes used as radiographic imaging agents. Further, these ligands or complexes can be covalently or non-covalently attached to biologically active carrier molecules, such as, antibodies, enzymes, peptides, peptidomimetics, hormones, and the like. The complexes of the present invention are prepared by reacting one of the aforementioned ligands with a radionuclide containing solution under radionuclide complex forming reaction conditions. In particular, if a technetium agent is desired, the reaction is carried out with a pertechnetate solution under technetium-99m complex forming reaction conditions. The solvent if different from water or saline may then be removed by any appropriate means, such as evaporation. The complexes are then prepared for administration to the patient by dissolution or suspension in a pharmaceutically acceptable vehicle.

The ligands of the present invention may be prepared from commercially available starting materials such as 2-aminomethyl imidazole, lysine, homoscrine lactone, glutamic acid, aminoadipic acid, mercaptoacetic acid, etc. by standard synthetic methods as described in the following Examples 1–2.

Radionuclide complexes according to the present invention may have the general formula:

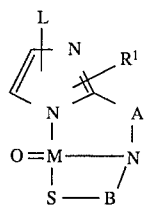

Formula (II)

wherein M represents an appropriate radionuclide, such as technetium or rhenium and wherein R¹, A, B, and L are as defined above in Formula (I).

In a preferred embodiment, a technetium radionuclide complex having the general Formula (II) may be formed from a pertechnetate solution and a ligand having the general Formula (I) above, wherein R¹ and L are hydrogen; A is

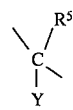

wherein R⁵ and Y are hydrogens; B is

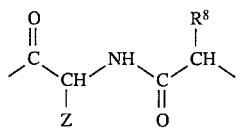

wherein R⁸ is hydrogen and Z is a —(CH₂)$_k$—X group wherein k is 4 and X is an amino, or an isothiocyanato group.

In another preferred embodiment, a technetium complex having the general Formula (II) may be formed from a pertechnetate solution and a ligand having the general Formula (I) above, wherein R¹ and L are hydrogen; A is

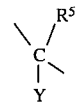

wherein R⁵ and Y are hydrogens; B is

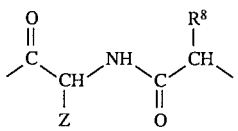

wherein R⁸ is hydrogen and Z is a —(CH₂)$_k$—X group wherein k is 2 and X is either carboxyl or hydroxyl.

The radionuclide containing solution may be obtained from radionuclide generators in a known manner. For example, when forming a technetium complex, the pertechnetate solution may be obtained from a technetium generator in a known manner. The radionuclide complex forming reaction is then carried out under appropriate reaction conditions. For example, the technetium 99m complex forming reaction is carried out under technetium complex forming temperatures, e.g. 20° C. to 100° C. for 10 minutes to several hours. The pertechnetate is used in technetium complex forming amounts, e.g. about 10⁻⁶ to 10⁻¹² molar amounts.

The present invention also relates to imaging agents containing a radionuclide complex as described above, in an amount sufficient for imaging, together with a pharmaceutically acceptable radiological vehicle. The radiological vehicle should be suitable for injection or aspiration, such as human serum albumin; aqueous buffer solutions, e.g tris(hydromethyl) aminomethane (and its salts), phosphate, citrate, bicarbonate, etc; sterile water; physiological saline; and balanced ionic solutions containing chloride and or dicarbonate salts or normal blood plasma cations such as Ca⁺², Na⁺, K⁺, and Mg⁺².

The concentration of the imaging agent according to the present invention in the radiological vehicle should be sufficient to provide satisfactory imaging, for example, when using an aqueous solution, the dosage is about 1.0 to 50 millicuries. The imaging agent should be administered so as to remain in the patient for about 1 to 3 hours, although both longer and shorter time periods are acceptable. Therefore, convenient ampules containing 1 to 10 mL of aqueous solution may be prepared.

Imaging may be carried out in the normal manner, for example by injecting a sufficient amount of the imaging composition to provide adequate imaging and then scanning with a suitable machine, such as a gamma camera.

The complexes according to the present invention may be prepared in accordance with the examples set forth below.

EXAMPLE 1

Preparation of 3,6-diaza-4-(2-hydroxy)ethyl-1-(S-tetrahydropyranyl)-mercapto-7-(2-imidazolyl)heptane.

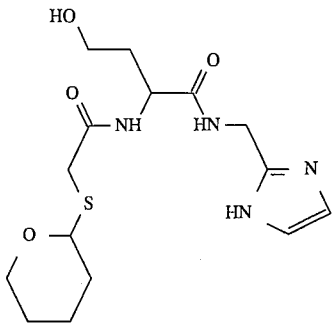

A mixture of 3-amino-5-aza-6-(2-imidazolyl)-4-oxohexan-1-ol (1.98 g, 0.01 mol) and (S-tetrahydropyranyl)m-ercaptoacetic acid N-succinimido ester (2.63 g, 0.01 mol) in acetonitrile (20 mL) was stirred at ambient temperature for 4 hours. The solvent was evaporated invacuo and the residue was purified by flash chromatography over reverse phase (50 g). Elution with water removed N-hydroxy succinimide along with low molecular weight impurities. Elution with water/methanol (3:2) followed by evaporation of the solvent furnished the desired ligand as pale tan foam. $^{13}$C-NMR (D$_2$O) δ 173.4, 172.7, 143.9, 121.1, 82.0, 65.2, 56.9, 50.7, 35.4, 32.6, 29.7, 28.2, 23.8, 20.4; thermal spray mass spectrum, m/Z 357 (M+1).

EXAMPLE 2

Preparation of technetium-99m complex of the ligand in Example 1.

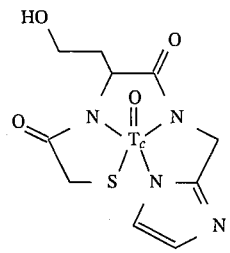

A solution of the ligand in Example 1 (110 μL of 1.0 mg/mL stock solution in 0.5 M sodium phosphate buffer, pH 8.0) was placed in a vial containing sodium gluconate (50 mg), and stannous chloride (0.5 mg). A solution of sodium pertechnetate in saline (1 mL) was then added and the entire mixture was heated in boiling water bath for 15 minutes. The product was purifed by reverse phase HPLC to give neutral $^{99m}$Tc(V) complex in about 50–60% yield.

The foregoing has been a discussion of the preferred embodiments of the present invention, but is not intended to limit the invention in any way. Rather, many modifications, variations and changes in detail may be made within the scope of the present invention.

What is claimed is:

1. A ligand useful in forming radionuclide complexes, said ligand having the general formula:

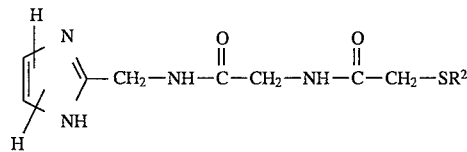

wherein R$^2$ is a benzoyl or a tetrahydropyranyl group.

* * * * *